United States Patent [19]

Moran et al.

[11] Patent Number: 4,550,166

[45] Date of Patent: Oct. 29, 1985

[54] (PYRIDINYL)-1,2,4-TRIAZOLO[4,3-A]PYRIDINES

[75] Inventors: Daniel B. Moran, Suffern, N.Y.; Dennis W. Powell, Greenwich, Conn.; Jay D. Albright, Nanuet, N.Y.

[73] Assignee: American Cyanamid Company, Stamford, Conn.

[21] Appl. No.: 612,188

[22] Filed: May 21, 1984

[51] Int. Cl.[4] ............................................. C07D 471/04
[52] U.S. Cl. ..................................................... 546/119
[58] Field of Search ...................... 546/119; 424/256

[56] References Cited

U.S. PATENT DOCUMENTS 4,242,515  12/1980  Trust et al. .......................... 546/119

OTHER PUBLICATIONS

"Burger's Medicinal Chemistry," Part II, 4th Ed., Manfred E. Wolff, ed., John Wiley & Sons, N.Y. (1981).

*Primary Examiner*—Henry R. Jiles
*Assistant Examiner*—Barbara Cassatt
*Attorney, Agent, or Firm*—Edward A. Conroy, Jr.

[57]  ABSTRACT

This disclosure describes novel substituted 1,2,4-triazolo[4,3-a]pyridines which possess anxioltic activity.

13 Claims, No Drawings

(PYRIDINYL)-1,2,4-TRIAZOLO[4,3-A]PYRIDINES

SUMMARY OF THE INVENTION

This invention relates to new organic compounds and more particularly, is concerned with novel 1,2,4-triazolo[4,3-a]pyridines and 3-alkyl-1,2,4-triazolo[4,3-a]pyridines which are substituted with 2-pyridinyl, 3-pyridinyl or 4-pyridinyl groups at either the 5, 6, 7 or 8 position, said compounds being anxiolytic agents which may be represented by the following structural formula:

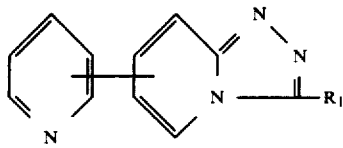

wherein $R_1$ is selected from the group consisting of hydrogen and lower alkyl($C_1$–$C_3$).

This invention is also concerned with a method of meliorating anxiety in mammals, with compositions of matter containing the above identified compounds and with processes for producing said compounds.

Of the above defined compounds, the most preferred ones are those having a methyl group in the 3 position and a 3-pyridinyl group at the 5, 6, 7 or 8 position.

DETAILED DESCRIPTION OF THE INVENTION

The novel compounds of this invention are generally obtained as white, tan, cream-colored or pale yellow crystalline solids having characteristic melting points and absorption spectra. They are appreciably soluble in organic solvents such as toluene, chloroform, dimethylformamide, ethyl acetate, lower alkanols and the like, but are relatively insoluble in water. The compounds of this invention are organic bases and form acid-addition salts with a variety of pharmacologically acceptable organic and inorganic acids. For the purposes of this invention the free bases are equivalent to their non-toxic, acid-addition salts.

The novel compounds of this invention may be prepared in accordance with the following general reaction schemes.

A 2-chloropyridine (2) containing a 2-, 3- or 4-pyridinyl substituent is reacted with hydrazine using pyridine as a solvent to give a 2-hydrazinopyridine (3). Ring closure of (3) to give 1,2,4-triazolo[4,3-a]pyridines (1) is carried out by reaction with a reagent represented by the formula (4), wherein $R_1$ is as defined hereinabove and X and Y are taken together to be that functionality which is capable of reacting with the terminal amino group in (3) to give the cyclic products (1). Examples of compounds of structure (4) include a carboxylic acid where X is oxygen and Y is hydroxy; an acid chloride where X is oxygen and Y is chloride; an amide where X is oxygen and Y is $NH_2$, $NHR_2$ or $NR_2R_3$, where $R_2$ and $R_3$ are lower alkyl($C_1$–$C_4$); and N,N-dialkylamide dialkylacetal where X is $(OR_4)_2$ and Y is $NR_2R_3$, where $R_2$, $R_3$ and $R_4$ are lower alkyl($C_1$–$C_4$); an ester where X is oxygen and Y is $OR_3$, where $R_3$ is lower alkyl($C_1$–$C_4$); an orthoester where X is $(OR_3)_2$ and Y is $OR_3$, where $R_3$ is lower alkyl($C_1$–$C_4$) and an anhydride where X is oxygen and Y is

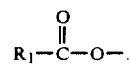

SCHEME I

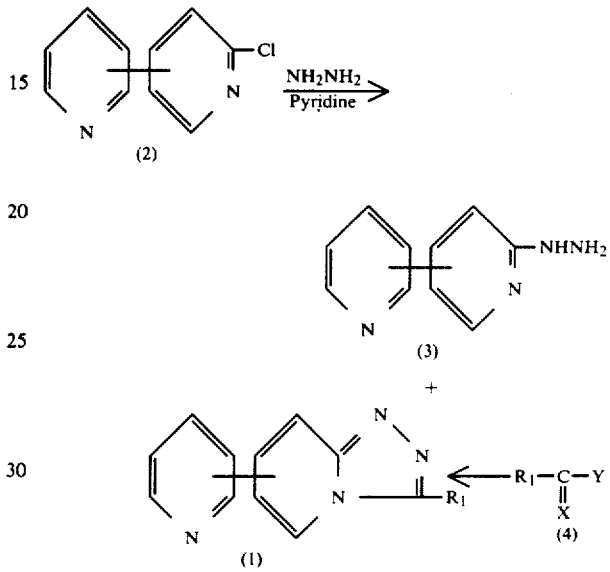

In accordance with the above reaction scheme I, an appropriately substituted 2-chloropyridine (2) is reacted with excess anhydrous hydrazine in refluxing pyridine for 1–5 days and the 2-hydrazinopyridine (3), either in a crude or purified form, is then reacted with a reagent represented by formula (4) to induce ring closure giving (1).

Especially preferred for ring closure are orthoesters [(4) where $X=(OR_3)_2$ and $Y=OR_3$] which react with 2-hydrazinopyridines (3) on heating with or without a solvent at 80°–130° C. The reaction may be carried out with catalytic amounts of glacial acetic acid. The appropriate 5-(pyridinyl)-2-chloropyridines (9) which are intermediates for the preparation of the compounds of this invention may be prepared as shown in reaction scheme II. For example, Vilsmeier formylation of 2-pyridylacetic acid, 3-pyridylacetic acid or 4-pyridylacetic acid with excess formylating reagent (prepared from dimethylformamide-phosphorus oxychloride, dimethylformamide-oxalyl chloride or dimethylformamide-thionyl chloride) affords the vinylogous amidinium salts (6). Condensation of the salts (6) [which in essence are 3-(pyridinyl)malondialdehyde equivalents] with t-butyl cyanoacetate in the presence of a base affords derivative (7). Ring closure of (7) with anhydrous hydrochloric acid in glacial acetic acid gives 2-chloropyridines (9) in a one step procedure which involves deblocking the carboxyl function, decarboxylation and cyclization of intermediate (8) to the 5-(pyridinyl)-2-chloropyridines (9).

SCHEME II

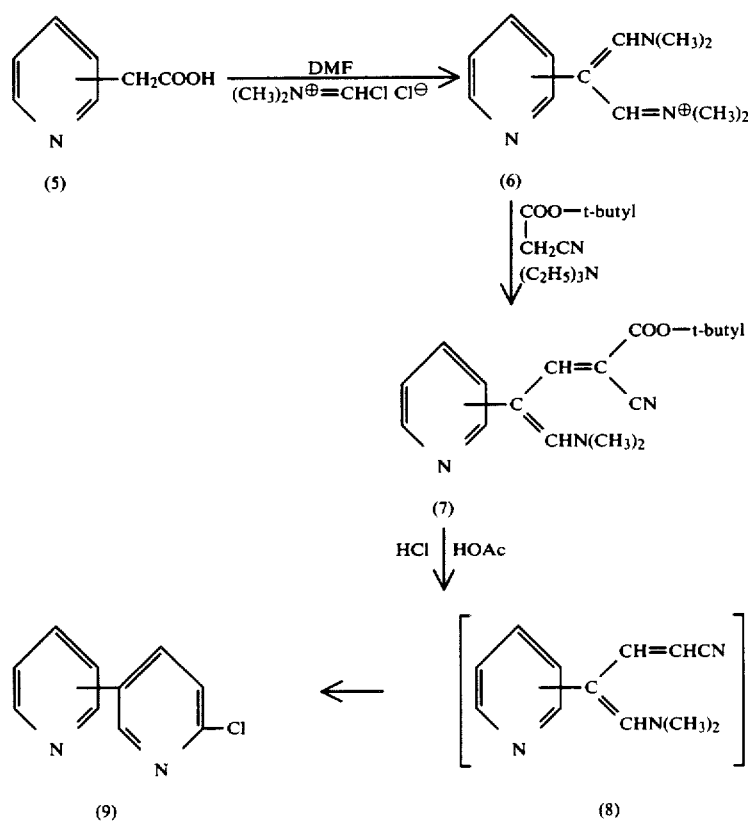

An alternative route to 5-(pyridinyl)-2-chloropyridines is shown in scheme III. The vinylogous amidinium salts (6) are hydrolysed in alkaline bases such as sodium hydroxide or potassium hydroxide to the aethylaminomethylene carboxaldehydes (10). Condensation of (10) with cyanoacetamide in alkanols with sodium alkoxides as base affords 5-(pyridinyl)-2(1H)-pyridinones (11). Hydrolysis of the cyano function with hydrochloric acid in acetic acid and decarboxylation in quinoline of the obtained acid derivatives (12) gives the 5-(pyridinyl)-2(1H)-pyridinones (13). Heating pyridinones (13) with phosphorus oxychloride gives 5-(pyridinyl)-2-chloropyridines (9). Reaction with hydrazine and ring closure affords the 6-(pyridinyl)-1,2,4-triazolo[4,3-a]pyridines (15).

SCHEME III

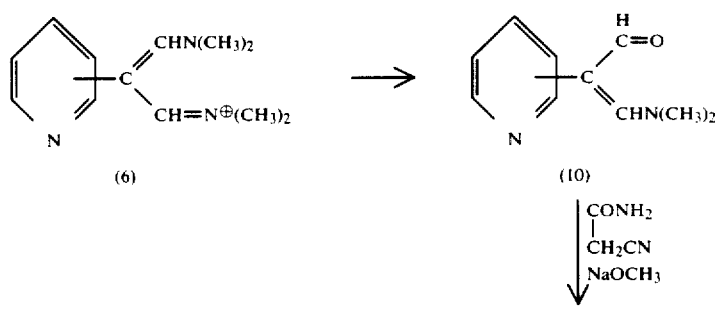

SCHEME III

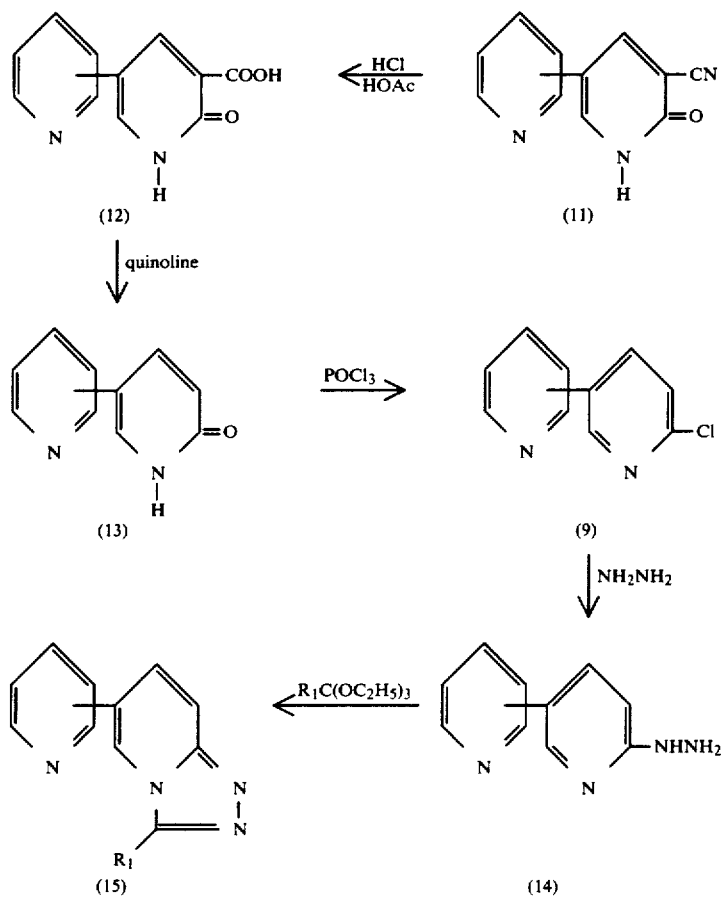

The appropriate 3-(pyridinyl)-2-chloropyridines (9) which are intermediates for the preparation of the compounds of the present invention may be prepared as shown in reaction scheme IV. For example, 2-, 3- or 4-pyridineacetonitriles (16) may be condensed with acetaldehyde with cesium carbonate as base to give α-ethylidene pyridineacetonitriles (17). These nitriles (17) are reacted with the dimethylformamide, dimethoxyacetal or similar dialkoxyacetals of dimethylformamide to give α-[3-(dimethylamino)-2-propenylidene]-pyridineacetonitriles (18). The preferred method for conversion of α-ethylidene pyridineacetonitriles (17) to derivatives (18) is by reaction with t-butoxy-bis-(dimethylamino)methane. Treatment of the α-[3-(dimethylamino)-2-propenylidene]pyrideneacetonitriles (18) with anhydrous hydrochloric or hydrobromic acid affords the 3-(pyridinyl)-2-chloropyridines (19) or the 3-(pyridinyl)-2-bromopyridines (21) which are useful intermediates to the novel 8-(pyridinyl)-1,2,4-triazolo[4,3-a]pyridines (22) of this invention.

SCHEME IV

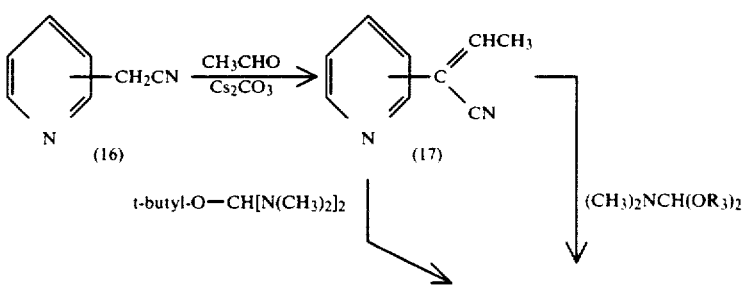

SCHEME IV

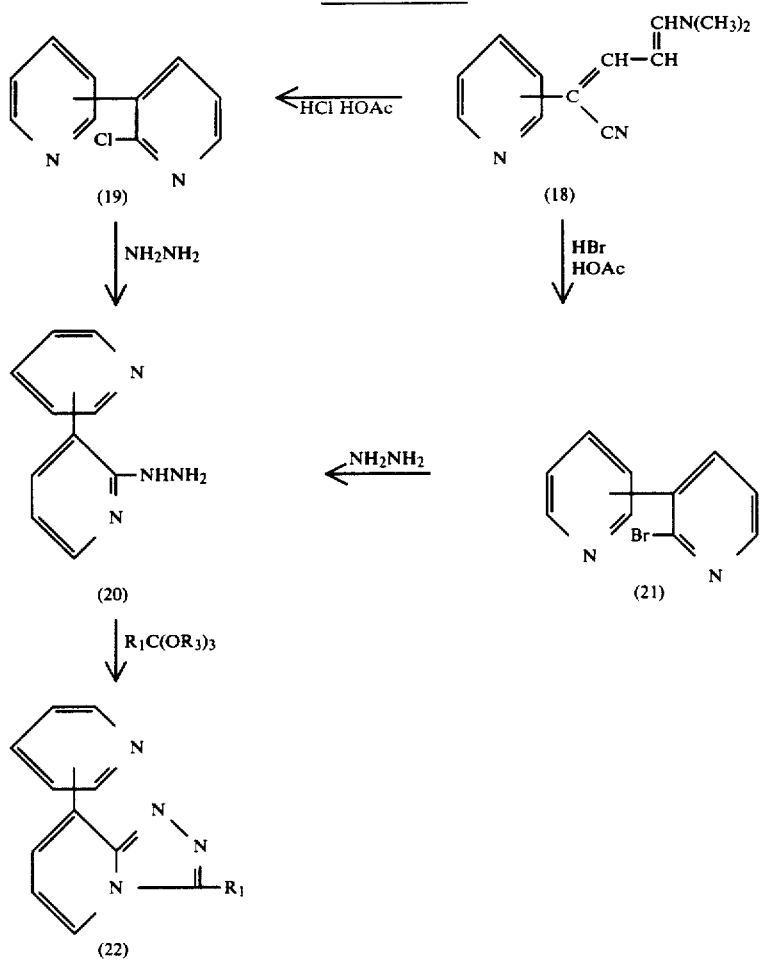

Alternative methods for preparing intermediate pyridinyl-2-chloropyridines involve the use of mono oxides of 2,2'-bipyridine, 2,4'-bipyridine, 3,3'-bipyridine, 4,4'-bipyridine, 2,3'-bipyridine and 3,4'-bipyridine. Typical reactions of these mono oxides to afford 2-chloropyridines are shown in scheme V. Illustrated are the synthesis of 3-methyl-(pyridinyl)-1,2,4-triazolo[4,3-a]pyridines of this invention which contain a 4-pyridinyl substituent (32), a 2-pyridinyl substituent (33) and a 3-pyridinyl substituent (34), (37) and (38).

SCHEME V

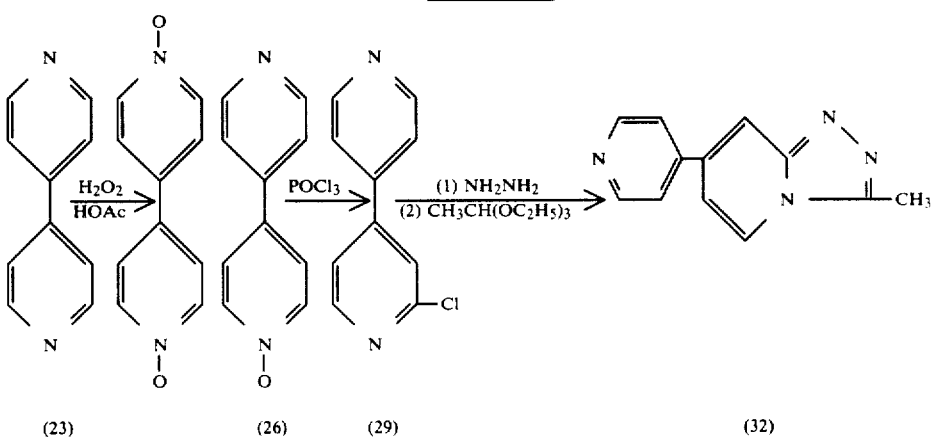

SCHEME V
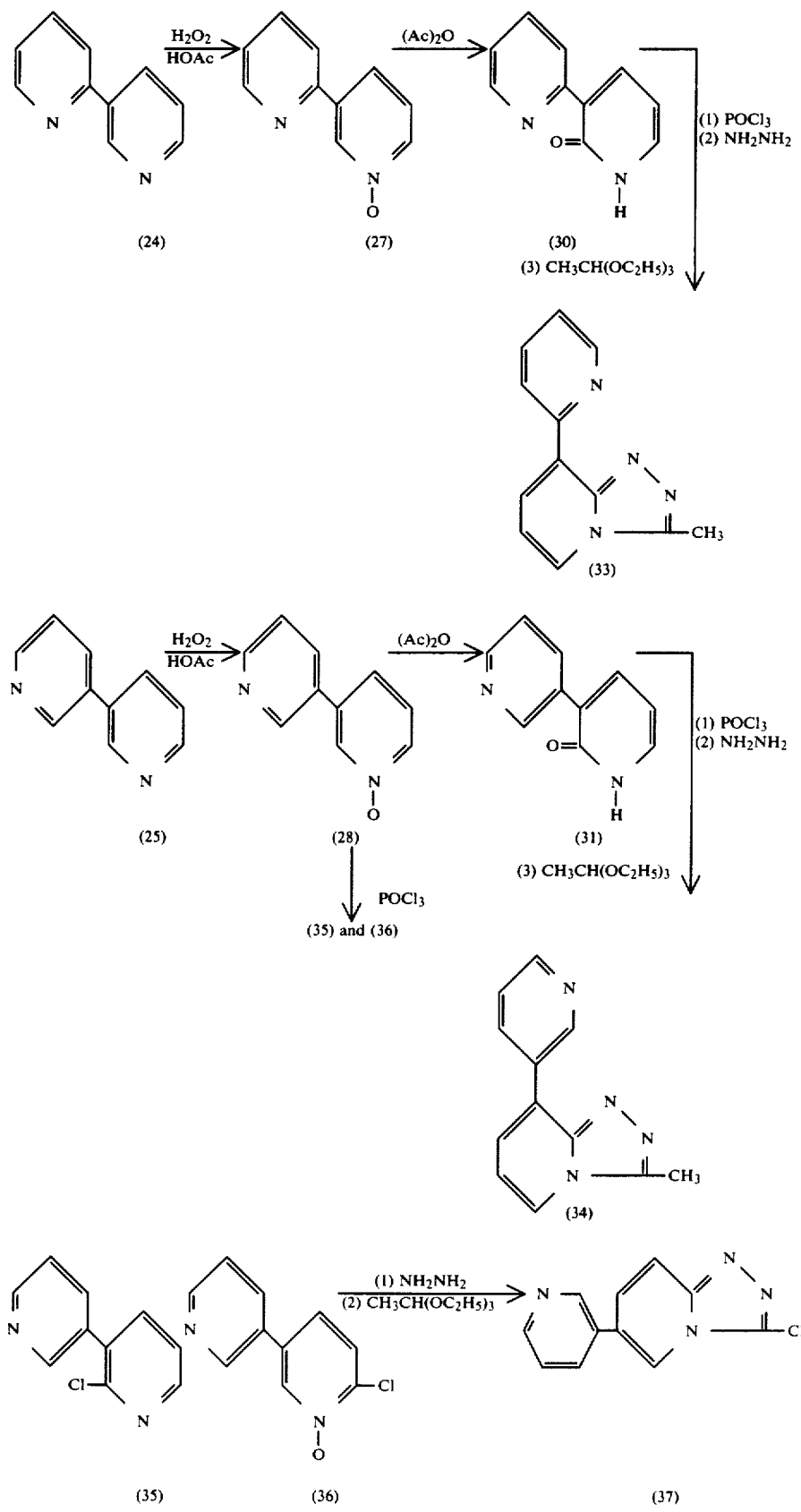

SCHEME V -continued

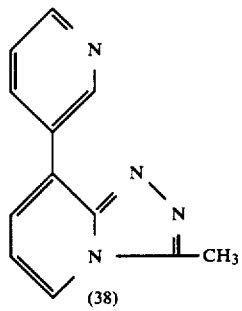

(38)

The novel compounds of this invention possess central nervous system activity at nontoxic doses and as such are useful as anxiolytic agents. That is, they produce certain responses in standard tests with laboratory animals which are known to correlate well with relief of anxiety in man.

The antianxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least four rats. At 30 or 60 minutes, the rats were treated intravenously with pentylenetetrazole at a dose of 23 mg/kg of body weight. This dose is estimated to cause clonic seizures in 99% of unprotected rats.

It has been reported [R. T. Hill and D. H. Tedeschi, "Animal Testing and Screening Procedures in Evaluating Psychotropic Drugs" in An Introduction to Psychopharmacology, Eds. R. R. Rech and K. E. Moore, Raven Press, New York, pp 237-288 (1971)] that there is a high degree of correlation between antagonism of pentylenetetrazole seizures in rats and antianxiety effects in higher warm-blooded animals.

The results of this test on representative compounds of this invention appear in Table I.

TABLE I

Protection Against Clonic Siezures Caused by Pentylenetetrazole in Rats

| Compound | Dose mg/kg | % of Rats Protected |
|---|---|---|
| 7-(2-pyridinyl)-1,2,4-triazolo[4,3-a]pyridine | 25 | 25 |
| 6-(3-pyridinyl)-1,2,4-triazolo[4,3-a]pyridine | 25 | 33 |
| 3-methyl-6-(3-pyridinyl)-1,2,4-triazolo[4,3-a]pyridine | 25 | 75 |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, pg 732 (April, 1977) and H. Mohler, et al., Science, 198, pg 849 (1977) was employed.

Male albino rats (Wistar strain, weighing 150-200 g each) were obtained from Royalhart Farms. $^3$H-Methyldiazepam (79.9 Ci/mmol) and $^3$H-methyl-flunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32 M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$ C.) until time of use. Frozen $P_2$ preparations were thawed and resuspended in four times the original homogenizing volume at time of assay.

The binding assay consisted of 300 $\mu$l of the $P_2$-fraction suspension (0.2-0.4 mg protein), 100 $\mu$l of test drug and 100 $\mu$l of $^3$H-diazepam (1.5 nM, final concentration) or $^3$H-flunitrazepam (1.0 nM, final concentration) which was added to 1.5 ml of 50 mM Tris.HCl (pH 7.4). Non-specific binding controls and total binding controls received 100 $\mu$l of diazepam (3 $\mu$M final concentration) and 100 $\mu$l of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials. After drying at 50°-60° C. for 30 minutes, 10 ml of Beckman Ready-Solve HP was added and the radioactivity determined in a Beckman Scintillation Counter.

Inhibition of binding was calculated by the difference between total binding and binding in the presence of test compound, divided by the total binding, $\times 100$.

The results of this test on representative compounds of this invention appear in Table II.

TABLE II

Inhibition of the Binding of $^3$H—Benzodiazepine to Brain-specific Receptors of Rats

| Compound | % Inhibition (1 $\mu$M) |
|---|---|
| 3-methyl-8-(3-pyridinyl)-1,2,4-triazolo[4,3-a]pyridine | 24 |
| 8-(2-pyridinyl)-1,2,4-triazolo[4,3-a]pyridine | 26 |
| 3-methyl-8-(2-pyridinyl)-1,2,4-triazolo[4,3-a]pyridine | 22 |
| 8-(3-pyridinyl)-1,2,4-triazolo[4,3-a]pyridine | 18 |
| 3-methyl-7-(2-pyridinyl)-1,2,4-triazolo[4,3-a]pyridine | 27 |

TABLE II-continued

| Inhibition of the Binding of ³H—Benzodiazepine to Brain-specific Receptors of Rats | |
|---|---|
| Compound | % Inhibition (1 μM) |
| 7-(2-pyridinyl)-1,2,4-triazolo[[4,3-a]-pyridine | 15 |
| 3-methyl-7-(4-pyridinyl)-1,2,4-triazolo-[4,3-a]pyridine, | 24 |
| 5-(2-pyridinyl)-1,2,4-triazolo[4,3-a]-pyridine | 26 |
| 6-(3-pyridinyl)-1,2,4-triazolo[4,3-a]-pyridine | 13 |
| 3-methyl-6-(3-pyridinyl)-1,2,4-triazolo-[4,3-a]pyridine | 20 |

Another test which has been used to assess antianxiety effects is a non-conditioned passive avoidance procedure described by J. R. Vogel, B. Beer and D. E. Clody, "A Simple and Reliable Conflict Procedure for Testing Antianxiety Agents", Psychopharmacologia, 21, 1–7 (1971). A conflict situation was induced in rats by a modification of this method.

Groups of 6 naive, Wistar strain rats, weighing 200–240 g each, were deprived of water for 48 hours and food for 24 hours. The test compounds were administered in single or graded, oral or intraperitoneal doses, suspended in a 2% starch vehicle containing 0.5% v/v polyethylene glycol and one drop of Polysorbate 80. Control animals received the vehicle alone. At 30 or 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group.

The test compounds are considered active if the number of shocks received by the test group is significantly higher than the control group by the Mann-Witney U test.

The results of this test on representative compounds of this invention appear in Table III.

TABLE III

| Non-Conditioned Passive Avoidance Test in Rats | | |
|---|---|---|
| Compound | Dose mg/kg | Result |
| 3-methyl-8-(3-pyridinyl)-1,2,4-triazolo-[4,3-a]pyridine | 25 | Active |
| 3-methyl-8-(2-pyridinyl)-1,2,4-triazolo-[4,3-a]pyridine | 25 | Active |

The novel compounds of the present invention have been found to be highly useful for drug therapy in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of nonvolatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Additionally, the active ingredient may be incorporated with the proper pharmaceutical carrier or carriers known in the art to produce a sustained-release tablet or capsule. Such compositions and preparations should contain at least 0.1% of active compound. The percentage of the compositions and preparations may, of course, be varied and may conveniently be between about 2% to about 60% of the weight of the unit. The amount of active compound in such therapuetically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The following non-limiting examples illustrate the preparation of representative compounds of the present invention.

EXAMPLE 1

3-Methyl-5-(2-pyridinyl)-1,2,4-triazolo[4,3-a]pyridine

A mixture of 51.55 g of 2,2'-bipyridine, 40 ml of 30% hydrogen peroxide and 250 ml of glacial acetic acid was heated for 18 hours, with the internal temperature kept at 70° C. by an I²R Therm-O-Watch automatic control. The solvent was removed under vacuum and the residue diluted with 100 ml of water. Solid potassium carbonate was added until the mixture was strongly alkaline. The mixture was extracted with chloroform in a liquid-liquid extractor for 18 hours. The organic extract was concentrated under vacuum, then the semi-solid was heated with ether and the mixture was filtered. The filtrate was concentrated to an oily solid which was chromatographed on a Waters Prep 500 column (silica gel) with ethyl acetate:hexane (1:3). After the impurities were eluted, the column was washed with ethyl acetate giving 16 g of an oil which solidified giving white crystals of 2,2'-bipyridine-2'oxide, mp 59°-61° C.

A mixture of 20.0 g of 2,2'-bipyridine-2'-oxide and 200 ml of acetic anhydride was refluxed for 18 hours. The volatiles were removed under vacuum and the residue heated on a steam bath with 200 ml of 5N sodium hydroxide for 6 hours. After treatment with activated carbon and filtration while hot, the mixture was allowed to cool and dichloromethane was added. Filtration gave a tan solid which was stirred in water and the pH adjusted to about 7.0 with dilute hydrochloric acid. Extraction with dichloromethane and concentration of the organic extracts gave a solid which was recrystallized from dichloromethane:hexane (99:1), giving 2-(2-pyridinyl)-6-(1H)-pyridinone as off-white crystals, mp 124°-127° C.

A mixture of 5.3 g of 2-(2-pyridinyl)-6-(1H)-pyridinone and 100 ml of phosphorus oxychloride was heated on a steam bath for 18 hours and then concentrated to dryness under vacuum. Crushed ice was added to the oil residue and the mixture made basic with solid potassium carbonate. The mixture was then extracted with dichloromethane, the extracts treated with activated carbon, filtered and concentrated, giving a solid which was purified by chromatography on silica gel with ethyl acetate as solvent, giving 4.1 g of 6'-chloro-2,2'-bipyridine as white crystals, mp 60°-62° C.

A mixture of 4.0 g of 6'-chloro-2,2'-bipyridine and 10 ml of anhydrous hydrazine in 50 ml of dry pyridine was refluxed for 48 hours. Additional hydrazine (10 ml) was added and the solution was refluxed for an additional 72 hours while 5 ml portions of hydrazine were added at 18 hour intervals. The volatiles were removed under vacuum, the residue dissolved in ether, dried over sodium sulfate and concentrated to a solid. This solid was recrystallized from ether-heptane, giving 3.0 g of 6'-hydrazino-2,2'-bipyridine as white crystals, mp 69°-70° C.

A mixture of 1.0 g of 6'-hydrazino-2,2'-bipyridine, 50 ml of ethyl orthoacetate and 5 drops of acetic acid was heated on a steam bath for 2.5 days. The volatiles were removed under vacuum and the residue crystallized from ether-hexane. These crystals were dissolved in dichloromethane and the solution passed through a short pad of hydrous magnesium silicate. Concentration of the filtrate gave 460 mg of the desired product as crystals, mp 168°-170° C.

EXAMPLE 2

5-(2-Pyridinyl)-1,2,4-triazolo[4,3-a]pyridine

A mixture of 1.2 g of 6'-hydrazino-2,2'-bipyridine and 7 ml of diethoxy methylacetate was stirred at 23° C. for 24 hours. The mixture was diluted with hexane and filtered. The crystals were recrystallized from ethyl acetate-hexane with the aid of activated carbon, giving 1 0 g of the desired product as white crystals, mp 120°-123° C.

EXAMPLE 3

3-Methyl-8-(3-pyridinyl)-1,2,4-triazolo[4,3-a]pyridine

A mixture of 57 g of 3-pyridineacetonitrile, 23.3 g of acetaldehyde and 0.5 g of cesium carbonate were dissolved in 1 liter of ethanol. The solution was stirred at 20° C. for 30 hours, then partitioned between 2 liters of water and 1 liter of ether. The aqueous phase was extracted with three 1 liter portions of ether and then 500 ml of ethyl acetate. All organic layers were combined, dried and the solvent removed at reduced pressure giving an orange oil. This oil was purified by chromatography on silica gel, eluting with ethyl acetate:hexane (1:1), giving a pale yellow oil which was crystallized from methylene chloride-hexane, giving α-ethylidene 3-pyridineacetonitrile as white needles, mp 46°-47° C.

A 0.2 g portion of α-ethylidene 3-pyridine acetonitrile and 0.315 ml of t-butoxy-bis-dimethylaminomethane were dissolved in tetrahydrofuran and stirred at 20° C. for 20 hours. The solvent was removed at reduced pressure and the orange oil was purified by chromatography, eluting with ethyl acetate:hexane (10:3). The eluate was concentrated to a solid which was recrystallized from methylene chloride-hexane, giving α-[3-(dimethylamino)-2-propenylidene]-3-pyridineacetonitrile as yellow crystals, mp 117°-120° C.

A 3.0 g portion of α-[3-(dimethylamino)-2-propenylidene]-3-pyridineacetonitrile was dissolved in 100 ml of glacial acetic acid. Dry hydrogen chloride gas (about 2.5 g) was introduced and the solution was heated at 60° C. for 3 hours. The reaction was cooled to 20° C. and then poured onto 200 g of ice. The solution was basified with potassium carbonate and then extracted with four 100 ml portions of methylene chloride. The organic extracts were combined, dried and the solvent removed at reduced pressure, giving an oil. This oil was dissolved in ethyl acetate:hexane (1:1) and passed through a pad of hydrous magnesium silicate. The solid obtained was recrystallized from hexane, giving 2-chloro-3,3'-bipyridine as white needles, mp 92°-93.5° C.

A 440 mg portion of 2-chloro-3,3'-bipyridine and 0.73 ml of anhydrous hydrazine were dissolved in 15 ml of pyridine and heated at 110° C. for 3 days. The volatiles were removed at reduced pressure, 10 ml of toluene was added and the volatiles again removed. The residue was partitioned between 125 ml of methylene chloride and 25 ml of saturated aqueous sodium carbonate. The organic layer was dried and the solvent removed at reduced pressure, giving an oily solid which was recrystallized from methylene chloride-hexane, giving 2-hydrazino-3,3'-bipyridine as a tan powder, mp 104.5°-107° C.

A 1.0 g portion of 2-hydrazino-3,3'-bipyridine was dissolved in 5 ml of triethyl orthoacetate and heated at 130° C. for 1.5 hours. The volatiles were removed at reduced pressure and the residue purified by chromatography on silica gel, eluting with ethyl acetate:methanol (9:2). The resulting solid was recrystallized from methylene chloride-hexane, giving the desired product as a tan powder, mp 112.5°-115° C.

EXAMPLE 4

8-(3-Pyridinyl)-1,2,4-triazolo[4,3-a]pyridine

A 4.15 g portion of 2-hydrazino-3,3'-bipyridine was dissolved in 30 ml of triethyl orthoformate and heated at 100° C. for 2 hours. The volatiles were removed at reduced pressure and the residue purified by chromatography on hydrous magnesium silicate, eluting with ethyl acetate. The solid was recrystallized from methylene chloride-hexane, giving 2.67 g of the desired product, mp 186°-189° C.

EXAMPLE 5

3-Methyl-6-(3-pyridinyl)-1,2,4-triazolo[4,3-a]pyridine

A 13.4 ml portion of N,N-dimethylformamide in 300 ml of methylene chloride was cooled to 0° C. An 11.1 ml portion of oxalyl chloride in 50 ml of methylene chloride was added dropwise over 10 minutes. The solution was allowed to warm to 20° C. and stirred for 30 minutes. The volatiles were removed at reduced pressure leaving a flocculent white powder. A 10.0 g portion of 3-pyridineacetic acid hydrochloride salt was added followed by 50 ml of N,N-dimethylformamide. This solution was stirred at 20° C. for 30 minutes and then warmed to 80° C. for 72 hours. The black solution was cooled to 20° C., 8.13 g of t-butyl cyanoacetate in 50 ml of N,N-dimethylformamide was added and the solution was cooled to 0° C. A 36 ml portion of triethylamine was added over 5 minutes and the solution was allowed to warm to 20° C. and was stirred for one hour. The solution was then poured onto 500 ml of water and extracted with three 150 ml portions of methylene chloride. The organic layers were combined, washed with brine, dried and the volatiles removed at reduced pressure. The residue was purified by chromatography, using a Waters 500 HPLC, two columns and eluting with acetone:hexane (2:3). The resulting oil was crystallized from ether-hexane, giving 1,1-dimethylethyl 2-cyano-5-(dimethylamino)-4-(3-pyridinyl)-2,4-pentanedienoate as yellow crystals, mp 161°-63° C.

An 18.9 g portion of 1,1-dimethylethyl 2-cyano-5-(dimethylamino)-4-(3-pyridinyl)-2,4-pentanedienoate was dissolved in 500 ml of glacial acetic acid. Dry hydrogen chloride gas (9.2 g) was bubbled into the solution which was then stirred at 20° C. for 72 hours. The volatiles were removed at reduced pressure and the black residue poured onto a mixture of 500 ml of ice/water and 200 ml of methylene chloride. The solution was basified to about pH 12 with potassium carbonate and then extracted with four 100 ml portions of methylene chloride. The organic layers were combined, dried and the volatiles removed at reduced pressure. The residue was purified by chromatography, using a Waters 500 HPLC, 2 columns and eluting with ethyl acetate:hexane (1:1). The obtained solid was recrystallized from methylene chloride-hexane, giving 6-chloro-3,3'-bipyridine as off-white crystals, mp 128°-130° C.

A 90 mg portion of 6-chloro-3,3'-bipyridine and 0.15 ml of anhydrous hydrazine were dissolved in 20 ml of pyridine and heated at 110° C. for 48 hours. The volatiles were removed at reduced pressure and the residue dissolved in 20 ml of triethyl orthoacetate and heated at 110° C. for 12 hours. The volatiles were removed at reduced pressure and the residue purified by chromatography on silica gel, eluting with ethyl acetate:methanol (9:2). The obtained tan solid was recrystallized from ethyl acetate-methanol, giving the desired product as off-white flakes, mp 199°-201.5° C.

EXAMPLE 6

6-(3-Pyridinyl)-1,2,4-triazolo[4,3-a]pyridine

As described in Example 5, 2.2 g of 6-chloro-3,3'-bipyridine was treated with 3.6 ml of anhydrous hydrazine in pyridine at 115° C. for 48 hours. The resulting crude 6-hydrazino-3,3'-bipyridine was dissolved in 25 ml of triethyl orthoformate and 2 drops of acetic acid and heated to 130° C. for 10 hours. The volatiles were removed at reduced pressure and the residue purified by chromatography on silica gel, eluting with ethyl acetate:methanol (9:2). The obtained solid was recrystallized from ethyl acetate-methanol, giving the desired product, mp 200°-202.5° C.

EXAMPLE 7

3-Methyl-5-(2-pyridinyl)-1,2,4-triazolo[4,3-a]pyridine

A mixture of 20 g of 2,2'-bipyridine-2'-oxide and 200 ml of acetic anhydride was refluxed for 18 hours and then concentrated under vacuum. The residue and 200 ml of 5N sodium hydroxide was heated on a steam bath for 6 hours, then treated with activated carbon and filtered rapidly while hot. Cooling and the addition of methylene chloride produced a solid which was collected and washed with methylene chloride. This solid was suspended in water, diluted with dilute hydrochloric acid to pH 7.0 and then extracted with methylene chloride. The extract was dried, the volatiles evaporated and the residue crystallized from methylene chloride-hexane and then ethyl acetate with the aid of activated carbon, giving 5.3 g of [2,2'-bipyridin]-6(1H)-one as white crystals, mp 126°-128° C.

To 100 ml of phosphorus oxychloride, cooled in an ice bath, was added 5.3 g of [2,2'-bipyridin]-6(1H)-one. The mixture was warmed to room temperature and then heated on a steam bath for 18 hours, then concentrated under vacuum. Crushed ice was added to the residual oil and the solution was basified with solid potassium carbonate. This mixture was extracted with methylene chloride, the extract was dried and evaporated in vacuo

EXAMPLE 8

3-Methyl-7-(2-pyridinyl)-1,2,4-triazolo[4,3-a]pyridine

A mixture of 23.0 g of 2,4'-bipyridine, 17.0 ml of 30% hydrogen peroxide and 100 ml of glacial acetic acid was stirred and heated for 48 hours with the internal temperature kept at 70° C. The solvent was removed under vacuum, the residue diluted with water and made alkaline with solid potassium carbonate. This mixture was extracted with chloroform in a liquid-liquid extractor and the extract concentrated to a solid. Acetone was added and the insoluble crystals removed by filtration. The acetone filtrate was chromatographed on a Waters-Prep-500 column and eluted first with acetone and then with methanol:acetone (1:9). Fractions showing one spot by TLC were combined and concentrated, giving 12.2 g of 2,4'-bipyridine-4'-oxide as off-white crystals, mp 114°–117° C.

A mixture of 2.0 g of 2,4'-bipyridine-4'-oxide and 50 ml of phosphorus oxychloride was heated on a steam bath for 18 hours and then concentrated under vacuum. Crushed ice was added to the residue and the mixture made alkaline with solid potassium carbonate. The solution was extracted with ethyl acetate, the extract dried, treated with activated carbon and passed through a short pad of hydrous magnesium silicate. The pad was washed with ethyl acetate and the filtrate concentrated, giving a solid which was recrystallized from methylene chloride-hexane, giving 1.3 g of 2'-chloro-2,4'-bipyridine as off-white crystals, mp 80°–81° C.

A mixture of 5.0 g of 2'-chloro-2,4'-bipyridine, 5 ml of anhydrous hydrazine and 100 ml of pyridine was refluxed. Additional 5 ml portions of anhydrous hydrazine were added after 18, 36 and 54 hours of refluxing. The solution was then refluxed for an additional 48 hours and the solvent removed under vacuum. The solid was dissolved in methylene chloride, treated with activated carbon, filtered and the filtrate concentrated to dryness. The residue was triturated with hexane, giving crystals which were recrystallized from methylene chloride-hexane, giving 2'-hydrazino-2,4'-bipyridine as yellow crystals, mp 120°–121° C.

A mixture of 2.0 g of 2'-hydrazino-2,4'-bipyridine and 50 ml of triethyl orthoacetate was heated on a steam bath for 18 hours, then chilled, filtered and the crystals washed with hexane. These crystals were recrystallized from methylene chloride, giving 1.8 g of the desired product as white crystals, mp 239°–241° C.

EXAMPLE 9

7-(2-Pyridinyl)-1,2,4-triazolo[4,3-a]pyridine

A mixture of 2.0 g of 2'-hydrazino-2,4'-bipyridine and 50 ml of triethyl orthoformate was heated on a steam bath for 18 hours then chilled and filtered. The crystals were dissolved in methylene chloride, treated with activated carbon, filtered and the filtrate concentrated. Chilling and filtration gave 1.5 g of the desired product as cream colored crystals, mp 144°–145° C.

EXAMPLE 10

3-Methyl-7-(4-pyridinyl)-1,2,4-triazolo[4,3-a]pyridine

A mixture of 37.68 g of 4,4'-bipyridine, dihydrate, 25 g of 30% hydrogen peroxide and 150 ml of glacial acetic acid was stirred and heated for 18 hours, with the internal temperature kept at 70° C. The solution was concentrated to dryness under vacuum, diluted with 100 ml of water, made alkaline with solid sodium carbonate and extracted with chloroform in a liquid-liquid extractor for 18 hours. The chloforom layer was concentrated under vacuum to a solid which was placed in a Soxhlet thimble and extracted with hexane for 36 hours. The hexane extracted solid was suspended in 300 ml of cyclohexane and heated on a steam bath for ½ hour. The mixture was cooled to 23° C. and filtered, giving 13.5 g of 4,4'-bipyridine-4'-oxide as cream colored crystals, mp 174°–176° C.

To 100 ml of phosphorus oxychloride, cooled in an ice bath, was added 10.0 g of 4,4'-bipyridine-4'-oxide. The mixture was stirred one hour, then heated on a steam bath for 18 hours and concentrated under vacuum. To the residue was added crushed ice and solid potassium carbonate. The alkaline solution was extracted with chloroform and the extract dried, treated with activated carbon and passed through a pad of hydrous magnesium silicate. The filtrate was concentrated to a solid which was crystallized from methylene chloride-hexane, giving 5.0 g of 2-chloro-4,4'-bipyridine as white crystals, mp 193°–196° C.

A mixture of 1.3 g of 2-chloro-4,4'-bipyridine and 6.5 ml of anhydrous hydrazine in 40 ml of dry pyridine was refluxed for 24 hours under argon and then concentrated. The residue was dissolved in methylene chloride, treated with activated carbon and the solvent was removed giving an oil which was crystallized from ether-hexane-methylene chloride. A 1.3 g portion of these crystals of 2-hydrazino-4,4'-bipyridine was combined with 50 ml of triethyl orthoacetate and heated on a steam bath for 1 hour. After standing overnight, hexane was added and after further standing, crystals separated. These crystals were collected and recrystallized from acetonehexane, giving the desired product as off-white crystals, mp 223°–226° C.

EXAMPLE 11

7-(4-Pyridinyl)-1,2,4-triazolo[4,3-a]pyridine

A 1.0 g portion of 2-hydrazino-4,4'-bipyridine and 50 ml of triethyl orthoformate was refluxed 18 hours, then chilled and the crystals collected. These crystals were dissolved in acetone-ethyl acetate, treated with activated carbon, filtered and the filtrate concentrated while hexane was added. Cooling gave the desired product as white crystals, mp 194°–196° C.

EXAMPLE 12

3-Methyl-8-(2-pyridinyl)-1,2,4-triazolo[4,3-a]pyridine

A mixture of 25.78 g of 2,3'-bipyridine, 20 g of 30% hydrogen peroxide and 125 ml of glacial acetic acid was stirred at 70° C. for 18 hours, then concentrated under vacuum and the residue dissolved in 50 ml of water. Solid potassium carbonate was added until the solution was strongly alkaline. The solution was then extracted with chloroform in a liquid-liquid extractor for 18 hours. The extract was treated with activated carbon and passed through a short pad of hydrous magnesium silicate. The filtrate was concentrated to an oil which crystallized on additon of pentane. These crystals were extracted with boiling cyclohexane giving grey crystals which were heated with acetone and filtered to remove insoluble material. The acetone filtrate was concentrated to 75 ml and allowed to stand. The resulting crystals were collected and purified by chromatography on silica gel, eluting with chloroform:ethanol (1:1). The resulting crystals were recrystallized from acetone-hexane, giving 6.0 g of 2,3-bipyridine-3'-oxide as white crystals, mp 78° C.

A mixture of 3.0 g of 2,3'-bipyridine-3'-oxide and 150 ml of acetic anhydride was refluxed 18 hours and the solvent removed under vacuum. The residue was dissolved in methanol, treated with activated carbon, filtered and the solvent removed. The residue was crystallized from methylene chloride-hexane, giving 2.2 g of 3-(2-pyridinyl-2(1H)-pyridinone as yellow crystals, mp 149°–150° C.

A 5.9 g portion of 3-(2-pyridinyl)-2(1H)-pyridinone in 100 ml of phosphorus oxychloride was heated on a steam bath for 18 hours, then concentrated under vacuum. The residue was stirred with crushed ice and chloroform and adjusted to pH 7 with 10N sodium hydroxide. The organic layer was separated, dried, filtered through a short pad of hydrous magnesium silicate and the filtrate concentrated under vacuum to an oil. This oil was heated with hexane, filtered while hot and the filtrate cooled to room temperature, giving 3.5 g of 2'-chloro-2,3'-bipyridine as white needles, mp 50° C.

A mixture of 0.5 g of 2'-chloro-2,3'-bipyridine, 5 ml of anhydrous hydrazine and 50 ml of dry pyridine was refluxed for 24 hours, then concentrated under vacuum and the residue dissolved in methylene chloride. The solution was dried and passed through a short pad of hydrous magnesium silicate. The filtrate was concentrated under vacuum to a gum which is 2'-hydrazino-2,3'-bipyridine. To this gum was added 50 ml of triethyl orthoacetate, the mixture was heated on a steam bath for 2.5 hours and concentrated under vacuum. The residue was dissolved in methylene chloride and while boiling, hexane was added. Cooling gave crystals which were recrystallized from methylene chloride-hexane, giving the desired product, mp 142°–143° C.

EXAMPLE 13

8-(2-Pyridinyl)-1,2,4-triazolo[4,3-a]pyridine

A mixture of 2.5 g of 2'-chloro-2,3'-bipyridine, 12.6 ml of anhydrous hydrazine and 50 ml of pyridine was refluxed for 36 hours and concentrated under vacuum to a gum. The gum was dissolved in methylene chloride, treated with activated carbon, dried over sodium sulfate and the solvent removed. The residue was crystallized from etherhexane to give 2.1 g of 2'-hydrazino-2,3'-bipyridine as yellow crystals, mp 64°–65° C.

A mixture of 1.7 g of 2'-hydrazino-2,3'-bipyridine and 50 ml of triethyl orthoformate was heated on a steam bath for 3 hours. Standing and chilling gave crystals which were collected, washed with hexane and dried, giving 1.5 g of the desired product as cream colored crystals, mp 212°–214° C.

EXAMPLE 14

8-(3-Pyridinyl)-1,2,4-triazolo[4,3-a]pyridine

A mixture of 4.15 g of 2-hydrazino-3,3'-bipyridine and 30 ml of triethyl orthoformate was heated at 100° C. for 2 hours. The volatiles were removed under vacuum and the residue placed on a short pad of hydrous magnesium silicate and eluted with ethyl acetate. The product was eluted with methanol. The methanol was removed under vacuum, the residue dissolved in methylene chloride, dried and the methylene chloride boiled off while hexane was added. Chilling and filtration gave 2.67 g of off-white crystals of the desired product, mp 186°–189° C.

EXAMPLE 15

3-Methyl-8-(3-pyridinyl)-1,2,4-triazolo[4,3-a]pyridine

A mixture of 15.6 g of 3,3'-bipyridine, 13.6 ml of 30% hydrogen peroxide and 100 ml of glacial acetic acid was stirred and heated for 18 hours with the internal temperature kept at 70° C. The solvent was removed under vacuum and ice added to the residue. This mixture was made alkaline with 10N sodium hydroxide and extracted with chloroform in a liquid-liquid extractor. The extract was concentrated under vacuum and the residual solid heated with 600 ml of acetone. Filtration and concentration of the filtrate gave 6.5 g of 3,3'-bipyridine-3'-oxide as off-white crystals, mp 151°–153° C.

A mixture of 3.0 g of 3,3'-bipyridine-3'-oxide and 100 ml of acetic anhydride was refluxed for 5 hours. The solvent was removed under vacuum, toluene was added, then removed and the residue was dissolved in chloroform and passed through a short pad of hydrous magnesium silicate. The filtrate was concentrated and hexane added while boiling off the solvent. Chilling and filtration gave a solid which was recrystallized twice from isopropanol giving 3-(3-pyridinyl)-2-(1H)-pyridinone as off-white crystals, mp 189°–192° C.

A mixture of 0.30 g of 3-(3-pyridinyl)-2(1H)pyridinone and 10 ml of phosphorus oxybromide was heated on a steam bath for 18 hours, then poured onto crushed ice and made alkaline with 10N sodium hydroxide. The resulting solid was collected, dissolved in methylene chloride and the solution passed through a short pad of hydrous magnesium silicate. The filtrate was concentrated and while boiling diluted with hexane. Concentration and chilling gave 2'-bromo-3,3'-bipyridine as white crystals, mp 97°–98° C.

A mixture of 16.46 g of 2'-bromo-3,3'-bipyridine, 24 ml of anhydrous hydrazine and 500 ml of dry pyridine was heated at 100° C. for 3 days. The solvent was removed under vacuum, toluene was added and removed and the residue was partitioned between saturated aqueous sodium carbonate and methylene chloride. The organic layer was dried, the solvent removed under vacuum and the residue crystallized from methylene chloride-hexane, giving 2'-hydrazino-3,3'-bipyridine as tan crystals.

A mixture of 0.27 g of 2'-hydrazino-3,3'-bipyridine and 5 ml of triethyl orthoacetate was heated at 130° C. for 1.5 hours and the solvent removed. The residue was chromatographed on silica gel and eluted first with ethyl acetate:methanol (9:2), then with methanol to elute the product. This solid was recrystallized from methylene chloride-hexane giving the desired product as tan crystals, mp 112°–115° C.

EXAMPLE 16

3-Methyl-6-(3-pyridinyl)-1,2,4-triazolo[4,3-a]pyridine
and
3-Methyl-8-(3-pyridinyl)-1,2,4-triazolo[4,3-a]pyridine A mixture of 2.0 g of 3,3'-bipyridine-3'-oxide and 50 ml of phosphorus oxychloride was refluxed for 18 hours and then concentrated under vacuum. To the residue was added crushed ice and then solid potassium carbonate until the solution was strongly alkaline. The mixture was extracted with chloroform, the extract dried and passed through a short pad of hydrous magnesium silicate. The filtrate was concentrated to an oil which was dissolved in hexane, treated with activated carbon, concentrated and chilled. Filtration gave 700 mg of white crystals which were a mixture of 2'-chloro-3,3'-bipyridine and 6'-chloro-3,3'-bipyridine.

A 0.5 g portion of this mixture and 5 ml of anhydrous hydrazine in 50 ml of dry pyridine was refluxed for 3 days. The mixture was concentrated under vacuum to a gum which was added to 40 ml of triethyl orthoacetate and heated on a steam bath for 18 hours. Concentration under vacuum and chromatography on silica gel with methanol:chloroform (1:4) as solvent gave 0.5 g of a solid which was 40% 3-methyl-6-(3-pyridinyl)-1,2,4-triazolo[4,3a]pyridine and 60% 3-methyl-8-(3-pyridinyl)-1,2,4-triazolo[4,3-a]pyridine.

We claim:

1. A compound selected from the group consisting of those of the formula:

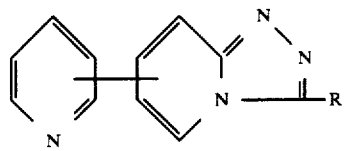

wherein R is hydrogen or alkyl ($C_1$-$C_3$) and the pharmacologically acceptable acid-addition salts thereof.

2. The compound according to claim 1; 3-methyl-5-(2-pyridinyl)-1,2,4-triazolo[4,3-a]pyridine.
3. The compound according to claim 1; 5-(2-pyridinyl)-1,2,4-triazolo[4,3-a]pyridine.
4. The compound according to claim 1; 3-methyl-8-(3-pyridinyl)-1,2,4-triazolo[4,3-a]pyridine.
5. The compound according to claim 1; 8-(3-pyridinyl)-1,2,4-triazolo[4,3-a]pyridine.
6. The compound according to claim 1; 3-methyl-6-(3-pyridinyl)-1,2,4-triaxolo[4,3-a]pyridine.
7. The compound according to claim 1; 6-(3-pyridinyl)-1,2,4-triazolo[4,3-a]pyridine.
8. The compound according to claim 1; 3-methyl-7-(2-pyridinyl)-1,2,4-triazolo[4,3-a]pyridine.
9. The coumpound according to claim 1; 7-(2-pyridinyl)-1,2,4-triazolo[4,3-a]pyridine.
10. The compound according to claim 1; 3-methyl-7-(4-pyridinyl)-1,2,4-triazolo[4,3-a]pyridine.
11. The compound according to claim 1; 7-(4-pyridinyl)-1,2,4-triazolo[4,3-a]pyridine.
12. The compound according to claim 1; 3-methyl-8-(2-pyridinyl-1,2,4-triazolo[4,3-a]pyridine.
13. The compound according to claim 1; 8-(2-pyridinyl)-1,2,4-triazolo[4,3-a]pyridine.

* * * * *